(12) United States Patent
Datta et al.

(10) Patent No.: US 11,298,084 B2
(45) Date of Patent: Apr. 12, 2022

(54) NON-INVASIVE METHOD AND SYSTEM FOR ESTIMATING BLOOD PRESSURE FROM PHOTOPLETHYSMOGRAM USING STATISTICAL POST-PROCESSING

(71) Applicant: Tata Consultancy Services Limited, Mumbai (IN)

(72) Inventors: Shreyasi Datta, Kolkata (IN); Anirban Dutta Choudhury, Kolkata (IN); Arijit Chowdhury, Kolkata (IN); Rohan Banerjee, Kolkata (IN); Tanushree Banerjee, Kolkata (IN); Arpan Pal, Kolkata (IN); Kayapanda Mandana, Kolkata (IN)

(73) Assignee: TATA CONSULTANCY SERVICES LIMITED, Maharashtra (IN)

( * ) Notice: Subject to any disclaimer, the term of this patent is extended or adjusted under 35 U.S.C. 154(b) by 333 days.

(21) Appl. No.: 15/900,774

(22) Filed: Feb. 20, 2018

(65) Prior Publication Data
US 2019/0069850 A1 Mar. 7, 2019

(30) Foreign Application Priority Data
Sep. 6, 2017 (IN) .............................. 201721031600

(51) Int. Cl.
*A61B 5/00* (2006.01)
*A61B 5/021* (2006.01)
(Continued)

(52) U.S. Cl.
CPC .......... *A61B 5/7267* (2013.01); *A61B 5/0077* (2013.01); *A61B 5/021* (2013.01);
(Continued)

(58) Field of Classification Search
CPC ....... A61B 5/00; A61B 5/7267; A61B 5/7246; A61B 5/7221; A61B 5/02116;
(Continued)

(56) References Cited

U.S. PATENT DOCUMENTS 6,662,032 B1 * 12/2003 Gavish ................. A61B 5/7275
600/323
9,259,186 B2 * 2/2016 Rodriguez-Llorente ....................
A61B 5/7203
(Continued)

OTHER PUBLICATIONS

Hedges and Shah, "Comparison of mode estimation methods and application in molecular clock analysis", 2003, BioMedCentral, 31, p. 1 (Year: 2003).*

(Continued)

*Primary Examiner* — Alex M Valvis
*Assistant Examiner* — Justin Xu
(74) *Attorney, Agent, or Firm* — Finnegan, Henderson, Farabow, Garrett & Dunner LLP (57) ABSTRACT

A system and method for estimating blood pressure (BP) using photoplethysmogram (PPG) has been explained. The PPG is captured from a PPG sensor (102). For preparing training model, a pulse oximeter is used for capturing PPG. For testing, a smartphone camera is used for capturing the PPG signal. A plurality of features are extracted from the preprocessed PPG signal. A BP distribution is then generated using the plurality of features and the training model. The BP distribution is part of a set of BP distributions generated from different subjects. Finally, a post-processing methodology have been used to reject inconsistent data out of the set of BP distributions and BP value is estimated only for the remaining BP distributions and a statistical average is provided as the blood pressure estimate.

6 Claims, 8 Drawing Sheets

(51) Int. Cl.
| | |
|---|---|
| *A61B 5/024* | (2006.01) |
| *A61B 5/1455* | (2006.01) |
| *G16H 50/20* | (2018.01) |
| *G16H 50/70* | (2018.01) |
| *G06K 9/00* | (2022.01) |
| *G16H 50/30* | (2018.01) |

(52) U.S. Cl.
CPC ...... *A61B 5/02116* (2013.01); *A61B 5/02416* (2013.01); *A61B 5/14552* (2013.01); *A61B 5/6898* (2013.01); *A61B 5/7203* (2013.01); *A61B 5/7221* (2013.01); *A61B 5/7246* (2013.01); *G16H 50/20* (2018.01); *A61B 2505/07* (2013.01)

(58) Field of Classification Search
CPC . A61B 5/02416; A61B 5/6898; A61B 5/7203; A61B 5/0077; A61B 5/14552; A61B 5/021; A61B 2505/07; A61B 5/7475; G16H 50/20; G16H 50/30; G06K 9/00536; G06K 9/00523; G06K 9/0051
See application file for complete search history.

(56) References Cited

U.S. PATENT DOCUMENTS

| | | | |
|---|---|---|---|
| 2007/0192129 A1* | 8/2007 | Fortuna | G06Q 99/00 705/1.1 |
| 2011/0224565 A1* | 9/2011 | Ong | A61B 5/7267 600/509 |
| 2013/0070792 A1 | 3/2013 | Shoaib et al. | |
| 2013/0197379 A1* | 8/2013 | Vepa | A61B 5/0245 600/513 |
| 2014/0128754 A1 | 5/2014 | Luna et al. | |
| 2015/0034541 A1 | 2/2015 | Cognetta et al. | |
| 2016/0166160 A1* | 6/2016 | Casale | A61B 5/7253 600/480 |
| 2016/0220188 A1 | 8/2016 | Chon et al. | |
| 2016/0324425 A1* | 11/2016 | Addison | A61B 5/4064 |
| 2017/0181649 A1* | 6/2017 | Carter | A61B 5/02108 |
| 2017/0360314 A1* | 12/2017 | Proenca | A61B 5/02125 |

OTHER PUBLICATIONS

Li et al. ("Characters available in photoplethysmogram for blood pressure estimation: beyond the pulse transit time", Australasian College of Physical Scientists and Engineers in Medicine, 2014) (Year: 2014).*

Hedges and Shah (2003, "Comparison of mode estimation methods and application in molecular clock analysis") (Year: 2003).*

Mun, Eun-Young & Eye, Alexanders. Bates, Marsha & Vaschillo, Evgeny. (2008). Finding Groups Using Model-Based Cluster Analysis: Heterogeneous Emotional Self-Regulatory Processes and Heavy Alcohol Use Risk. Developmental psychology. 44. 481-95. 10.1037/0012-1649.44.2.481 (hereinafter-Mun et al.). (Year: 2008).*

* cited by examiner

NON-INVASIVE METHOD AND SYSTEM FOR ESTIMATING BLOOD PRESSURE FROM PHOTOPLETHYSMOGRAM USING STATISTICAL POST-PROCESSING

PRIORITY CLAIM

This U.S. patent application claims priority under 35 U.S.C. § 119 to: India Application No. 201721031600, filed on Sep. 6, 2017. The entire contents of the aforementioned application are incorporated herein by reference.

TECHNICAL FIELD

The embodiments herein generally relates to the field of blood pressure estimation, and, more particularly, to a method and system for estimating the blood pressure using the photoplethysmogram (PPG) by applying statistical post processing techniques.

BACKGROUND

Blood pressure (BP) is considered to be an important biomarker for cardiac risk estimation. Irregular heartbeats, fluctuation of blood pressure (BP) or cholesterol levels are typically considered as biomarkers as well as risk indicators for stroke and cardiovascular diseases. Over the last few years, ubiquitous and continuous monitoring of the digital biomarkers have gained immense importance all over the world. They use wearable devices or smartphones to capture physiological information to estimate the markers through signal processing and data driven predictive analytics. 24×7 wearable monitors in the form of smart eyewear or wristbands can provide important health information without disrupting normal activities. On the other hand, smartphone based e-health monitors are not only unobtrusive and easy to use, they also come at no additional cost, thereby making them popular candidates for affordable healthcare.

The smartphone based e-health monitor uses smartphone camera to capture the variation in blood flow through Photoplethysmogram (PPG) that can be used to measure heart rate (HR) or BP. Besides being cost effective, smartphone PPG based BP estimation avoids the professional expertise in tracking the Korotkoff sounds required for cuff-based BP measuring devices and the attachment of any wearable sensor. However, though HR estimation from smartphone PPG has achieved success through efficient noise cleaning and signal processing, Systolic BP (SBP) and Diastolic BP (DBP) estimation have proved to be relatively difficult due to complex physiological processes involved.

In few prior art techniques, data driven models were proposed to predict BP from both smartphone and oximeter PPG signals. However, certain issues like 1) the experimental dataset to be of a wide range of BP (only subjects with normal BP were considered) and 2) unique subjects between the training and testing samples (this can create over-fitting by introducing person specific bias) were not addressed. In another technique, Windkessel Model based prediction of BP from PPG features via latent parameters were proposed and analyzed for different types of datasets. However, issues of the effects of noise on the performance for data collected in field and failure of predicting high BP were reported. The ultimate goal being smartphone deployment, issues like sensor agnostic PPG feature selection become significant. Additionally, smartphone PPG is challenging to work on because of its noisy nature. Even for a stable subject with no cardiac conditions, there can be a wide variation in features estimated per cardiac cycle leading to variation in BP estimated in a single session. Hence it is important to choose an appropriate statistical average to represent the BP estimated per session. It is well known that a simple arithmetic mean cannot be used as a suitable representative for any data distribution that has outliers. Median and mode are better representatives, and mode is favored more as it is less affected by outliers.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides a system for estimating blood pressure (BP) using photoplethysmogram (PPG). The system comprises a photoplethysmogram (PPG) sensor, a memory and a processor. The PPG sensor configured to capture photoplethysmogram (PPG) signal. The processor further comprises a preprocessing module, a feature selection module, a training model generation module, a regression module and a post-processing module. The preprocessing module preprocesses the captured PPG signal. The feature selection module extracts a plurality of features from the preprocessed PPG signal. The training model generation module creates a training model for estimating the blood pressure (BP) using the plurality of features and a ground truth value of the BP. The regression module generates a BP distribution using the training model, wherein the BP distribution is part of a set of BP distributions generated from different subjects. The post-processing module rejects unacceptable BP distributions out of the set of BP distributions based on a predefined criteria. The post processing module further provides a statistical average for the accepted BP distributions to estimate the blood pressure.

In another aspect, a method for estimating blood pressure (BP) using photoplethysmogram (PPG). Initially, photoplethysmogram (PPG) signal is captured using the PPG sensor. The PPG signal is then preprocessed using a preprocessing module. In the next step, a plurality of features are extracted from the preprocessed PPG signal. In the next step a training model is created for estimating the BP using the plurality of features of the PPG signal and a ground truth value of the BP. Further a BP distribution is generated using the training model, wherein the BP distribution is part of a set of BP distributions generated from different subjects. In the next step, unacceptable BP distributions out of the set of BP distributions are rejected based on a predefined criteria. And finally, a statistical average is provided for the accepted BP distributions to estimate the blood pressure.

In another aspect, a system for estimating blood pressure (BP) using photoplethysmogram (PPG) is provided. The system includes one or more memories; and one or more hardware processors, the one or more memories coupled to the one or more hardware processors wherein the one or more hardware processors are capable of executing programmed instructions stored in the one or more memories to: (a) capture a photoplethysmogram (PPG) signal using a PPG sensor (102); (b) preprocess the PPG signal using a preprocessing module (108); (c) extract a plurality of features from the preprocessed PPG signal; (d) create a training model for estimating the BP using the plurality of features of the PPG signal and a ground truth value of the BP; (e) generate a BP distribution using the training model, wherein the BP distribution is part of a set of BP distributions generated from different subjects; (f) reject unacceptable BP distributions out of the set of BP distributions based on a predefined criteria; and (g) provide a statistical average for the accepted BP distributions to estimate the blood pressure.

In yet another aspect, a non-transitory computer-readable medium having embodied thereon a computer program for executing a method for estimating blood pressure (BP) using photoplethysmogram (PPG). The method includes steps of: (a) capturing photoplethysmogram (PPG) signal using a PPG sensor (102); (b) preprocessing the PPG signal using a preprocessing module (108); (c) extracting a plurality of features from the preprocessed PPG signal; (d) creating a training model for estimating the BP using the plurality of features of the PPG signal and a ground truth value of the BP; (e) generating a BP distribution using the training model, wherein the BP distribution is part of a set of BP distributions generated from different subjects; (f) rejecting unacceptable BP distributions out of the set of BP distributions based on a predefined criteria; and (g) providing a statistical average for the accepted BP distributions to estimate the blood pressure.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

It is to be understood that both the foregoing general description and the following detailed description are exemplary and explanatory only and are not restrictive of the invention, as claimed.

BRIEF DESCRIPTION OF THE DRAWINGS

The embodiments herein will be better understood from the following detailed description with reference to the drawings, in which.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

GLOSSARY—TERMS USED IN THE EMBODIMENTS

The expression "photoplethysmogram" or "PPG" sensor in the context of the present disclosure refers to a sensor used to capture the photoplethysmogram signal of the subjects. For the purpose of generating the training model, pulse oximeter has been used as the PPG sensor. For testing purpose, the smartphone camera has been used to capture the PPG signal.

Referring now to the drawings, and more particularly to FIG. 1 through FIG. 7, where similar reference characters denote corresponding features consistently throughout the figures, there are shown preferred embodiments and these embodiments are described in the context of the following exemplary system and/or method.

Figure 1:
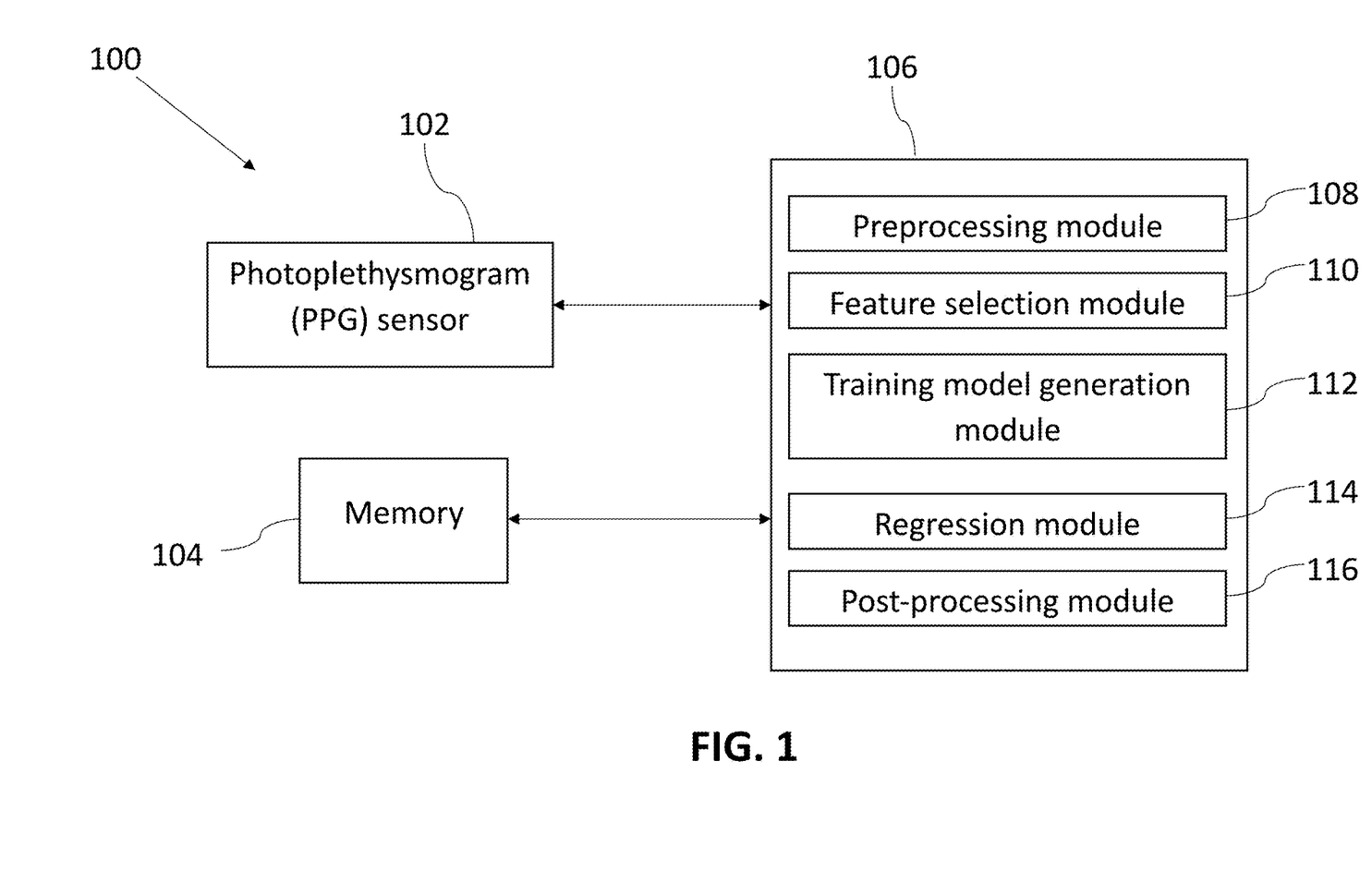
FIG. 1 illustrates a block diagram for estimating blood pressure (BP) using photoplethysmogram (PPG) according to an embodiment of the present disclosure.

According to an embodiment of the disclosure, a system 100 for estimating blood pressure (BP) using the photoplethysmogram (PPG) is shown in FIG. 1. The system 100 uses a smartphone photoplethysmogram (PPG) to predict blood pressure (BP) non-invasively. A post-processing methodology have been used to reject inconsistent data and predict BP values only for the remaining data. A statistical average across all BP values in a single session is provided as the blood pressure estimate.

According to an embodiment of the disclosure, the system 100 consists of a photoplethysmogram (PPG) sensor 102, a memory 104 and a processor 106 as shown in the block diagram FIG. 1. The processor 106 is in communication with the memory 104. The processor 106 is configured to execute algorithms stored in the memory 104. According to an embodiment of the disclosure, the processor 106 further includes a plurality of modules for performing various functions. The processor 106 may include a preprocessing module 108, a feature selection module 110, a training model generation module 112, a regression module 114 and a post processing module 116.

According to an embodiment of the disclosure, the PPG sensor 102 is a pulse oximeter or a smartphone camera. For generating the training model, the pulse oximeter was used for capturing the PPG signal. While for testing, the PPG was measured using the camera of the smartphone. As the smartphone PPG has very low signal-to-noise ratio, hence it poses a few additional challenges to extract information of complex physiological signals.

According to an embodiment of the disclosure, the system 100 includes the preprocessing module 108 to clean the PPG signal. The preprocessing module 108 is configured to remove noise from the PPG signal by performing band pass filtering and baseline correction. The band pass filtering is performed in the range of 0.75-8 Hz prior to a plurality of features extraction. Changes in PPG amplitude due to variable finger pressure and discontinuities due to motion artifacts are taken care of by implementing cycle selection on the basis of similar pulse height and periodicity.

According to an embodiment of the disclosure, the preprocessed PPG signal is then provided to the feature selection module 110. A plurality of features of the PPG signal are chosen from a time domain signal in such a way that the chosen features are independent of the PPG sensor 102. The plurality of features are selected after analyzing their linear correlation with respect to ground truth BP in the training dataset. Systolic upstroke time ($T_s$), diastolic time ($T_d$), systolic area ($A_s$) and diastolic area ($A_d$) are typical characteristics of the PPG waveform. In the present embodiment, the ultimate goal is to find features that have relation with BP in both oximeter and smartphone data. Ratios of PPG features like $T_s/T_d$ and $A_s/A_d$ were chosen as they were stable even in smartphone PPG. A similar linear correlation evaluation was also carried between PPG features and ground truth BP, thereby selecting $T_s$, $T_s/T_d$, $A_s/A_d$, $1/T_s^2$, Age and Body Mass Index (BMI).

According to an embodiment of the disclosure, the training model generation module 112 generates a training model for estimating the BP. The training model is generated using the plurality of features of the PPG signal and the ground truth value of the BP. Further, the regression module 114 is configured to generate a BP distribution per session using the training model. The BP distribution is part of a set of BP distributions generated from different subjects. A gradient descent learning based linear regression is used to create a training model from the selected features and the corresponding ground truth. A direct linear regression model is created on the PPG features for BP estimation, avoiding the latent parameters, to make a simpler system, easier to run as a mobile application.

According to an embodiment of the disclosure, the post processing is performed on the set of BP distributions by the post processing module 116. The post processing results in the rejection of unacceptable BP distributions out of the set of BP distributions based on a predefined criteria. The predefined criteria includes clustering the estimated BP distributions and rejecting those BP distributions where there are i) multiple equally dominant clusters ii) two clusters that are too far apart or iii) unacceptable cluster formation. The post processing module 116 is further configured to provide the statistical average for the accepted BP distributions to estimate the blood pressure.

Figure 2:
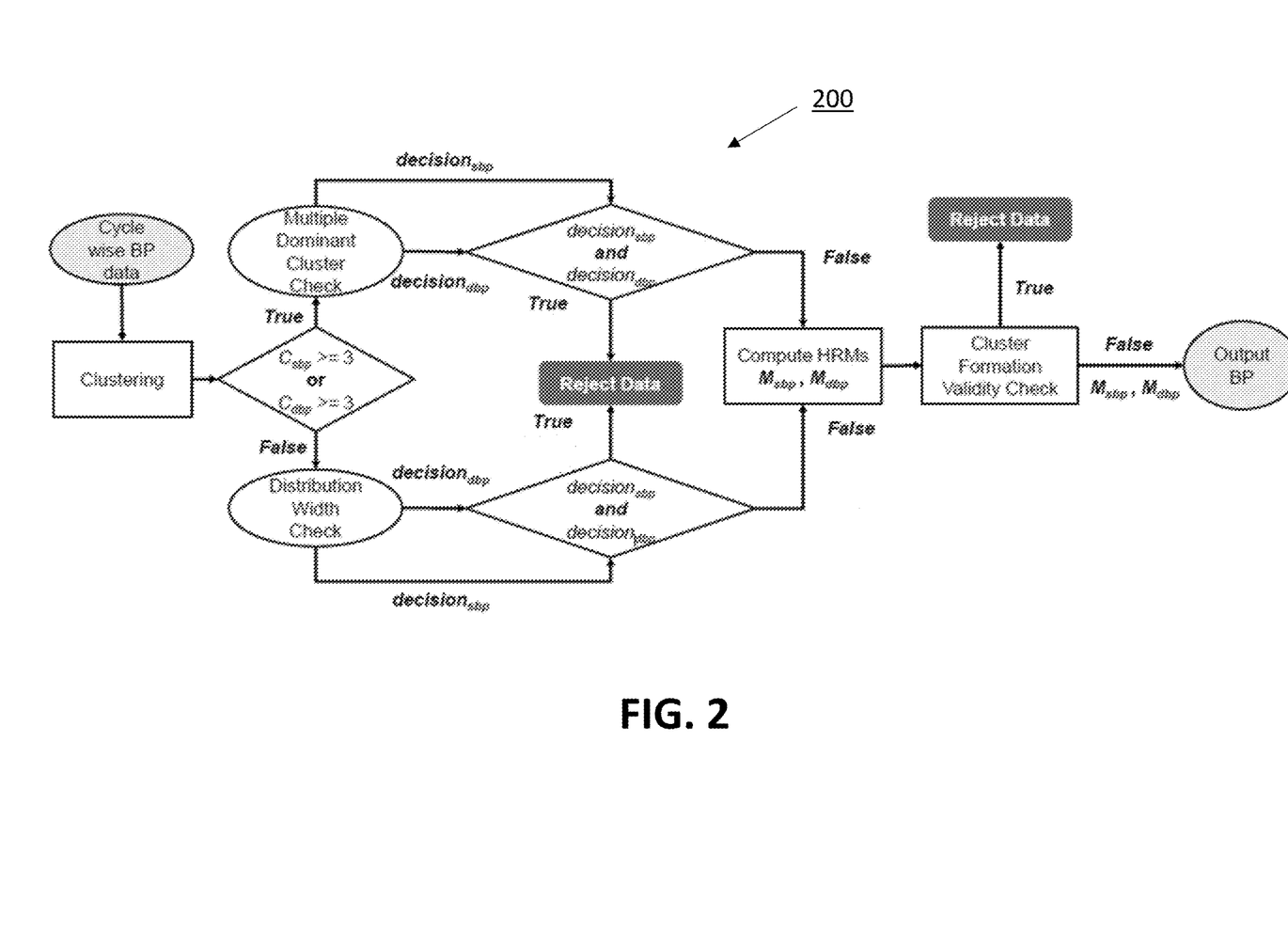
FIG. 2 shows a flowchart depicting the steps involved in the post processing of the plurality of BP distributions according to an embodiment of the present disclosure.

A flowchart 200 illustrating the steps involved in the post processing of the plurality of BP distributions is shown in FIG. 2. The first step is clustering the cycle-wise BP distributions into clusters of similar BP based on probability density. For this purpose, the 'mclust' package of R is used. It provides parameter estimation via the Expectation Maximization algorithm for normal mixture models and chooses clusters on the basis of the best Bayesian Information Criterion (BIC).

Figure 3:
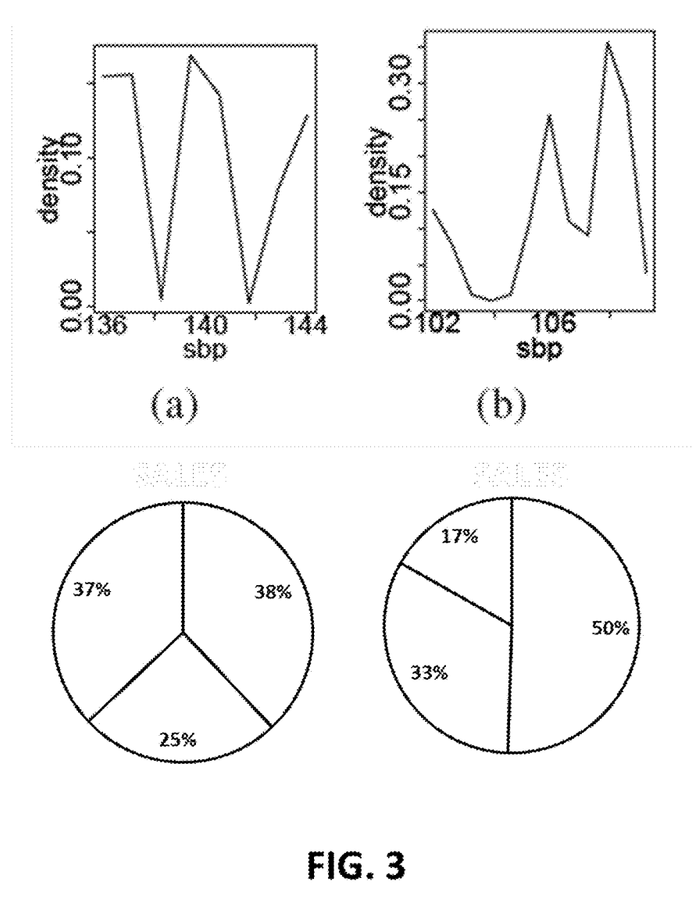
FIG. 3 shows the multiple dominant cluster check for the plurality of BP distributions according to an embodiment of the present disclosure

Further, multiple dominant clusters are checked, This module is traversed when the number of clusters in systolic blood pressure, SBP ($C_{sbp}$) or diastolic blood pressure, DBP ($C_{sbp}$) are greater than or equal to 3. It may happen that too many small clusters exist uniformly all over the distribution as shown in FIG. 3. This indicates that estimated BP is varying highly over the session and hence is unacceptable. As demonstrated in Algorithm 1 below, if the range of cluster populousness of multiple clusters is below a threshold, the session is considered to have multiple equally dominant clusters and hence it is to be rejected. Here populousness of the $i^{th}$ cluster is given by $n_i/N$, where $n_i$ and N are the number of elements in $i^{th}$ cluster and the total number of elements respectively.

| Algorithm 1: Multiple Dominant Cluster Check |
| --- |
| 1:   procedure is_multiple_dominant_cluster($num_{bp}$) |
|       ▷ $num_{bp}$: vector of cluster sizes for BP distribution |
| 2:     $C_{bp}$ = length ($num_{bp}$) |
| 3:     decision = false |
| 4:     if $C_{bp}$ >= 3 then |
| 5:         $range_{bp}$ = |
| 6:         (max($num_{bp}$) − min($num_{bp}$))/sum($num_{bp}$) |
| 7:         if $range_{bp}$ <= 0.3 then |
| 8:            decision = true |
| 9:         end if |
| 10:    end if |
| 11:    return decision |
| 12:  end procedure |

Figure 4:
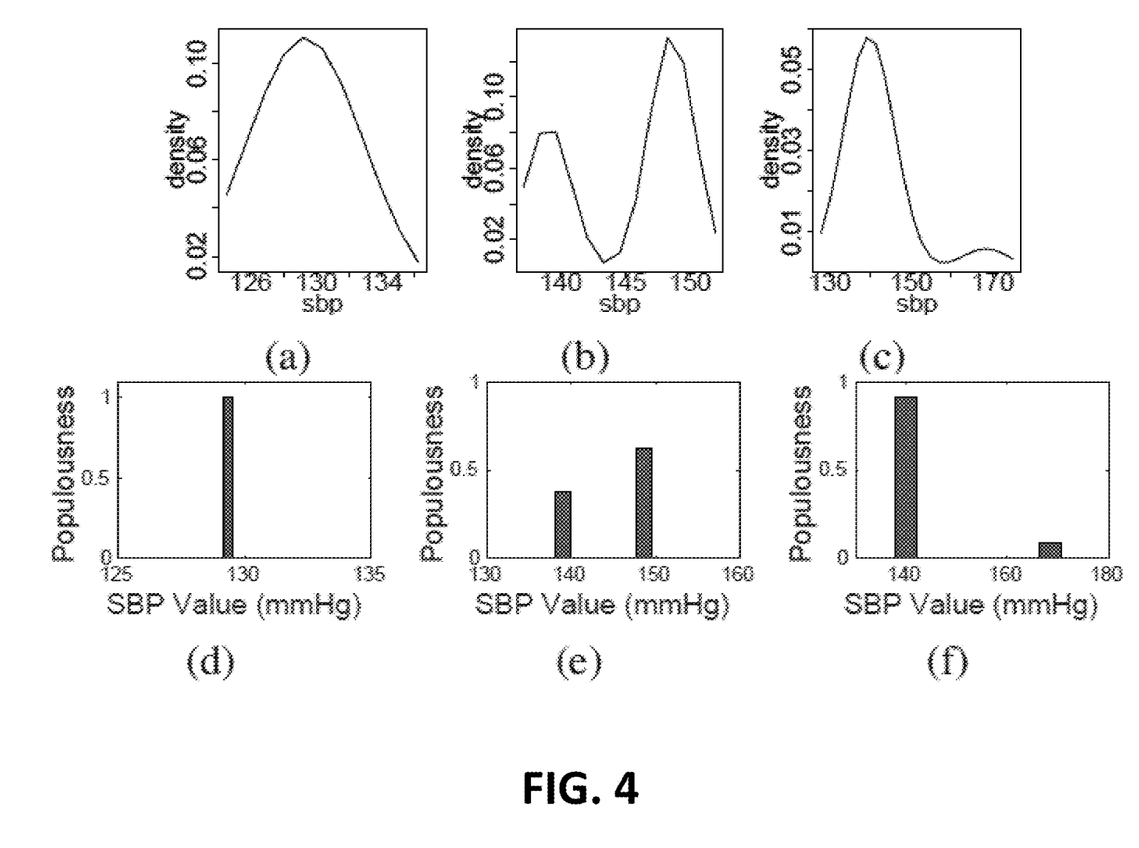
FIG. 4 shows the distribution width check for the plurality of BP distributions according to an embodiment of the present disclosure.

In the next step, the distribution width is checked. The inputs to this block are the distributions having one or two clusters. If there is a single cluster, it is accepted. In resting condition, BP cannot usually vary too much. Hence, as shown in Algorithm 2 below, the sessions were rejected where the difference of the two cluster means (in case of 2 clusters) is equal to or more than 15 mmHg as shown in FIG. 4. In case the distribution is found suitable to work on, as decided by both the above cluster check modules, Half Range Mode (HRM), which iteratively uses densest half ranges for mode computation is used as the statistical average. HRMs $M_{sbp}$ and $M_{dbp}$ are computed for the distributions of SBP and DBP respectively as the required statistical averages.

| Algorithm 2: Distribution Width Check |
| --- |
| 1:   procedure is_wide_distribution($mean_{bp}$) |
|       ▷ $mean_{bp}$: vector of cluster means for BP distribution |
| 2:     $C_{bp}$ = length($num_{bp}$) |
| 3:     decision = false |
| 4:     if $C_{bp}$ == 1 then |
| 5:         decision = false |
| 6:     else |
| 7:         if max($mean_{bp}$) − min($mean_{bp}$) < 15 then |
| 8:            decision = false |
| 9:         else |
| 10:           decision = true |
| 11:        end if |
| 12:    end if |
| 13:    return decision |
| 14:  end procedure |

Finally the cluster formation validity is checked. Upon investigation of the output of the clustering module, it was found that for some data, the cluster log likelihood value was too negative, indicating a possibility of invalid cluster formation. Hence this data was rejected.

Figure 5A:
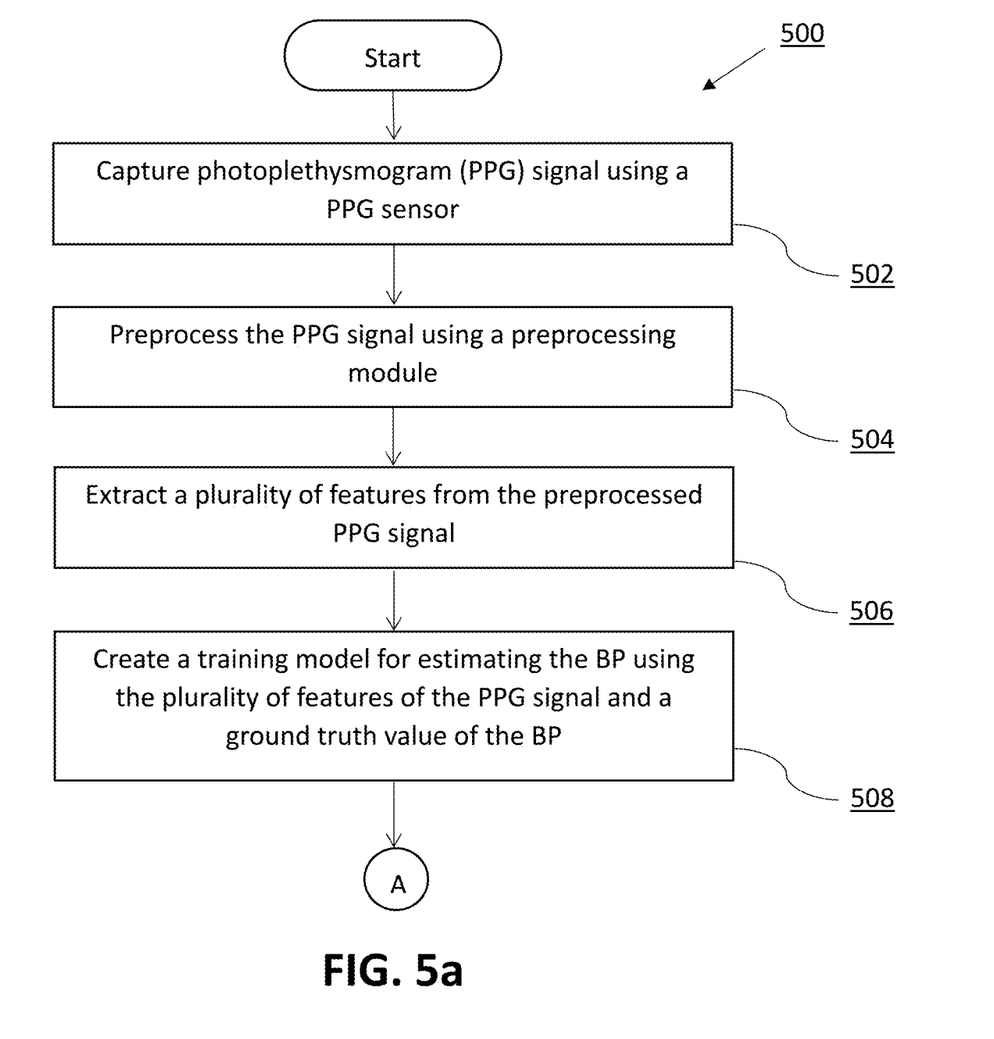
FIG. 5a-5b is a flowchart illustrating the steps involved for estimating blood pressure (BP) using photoplethysmogram (PPG) according to an embodiment of the present disclosure.
Figure 5B:
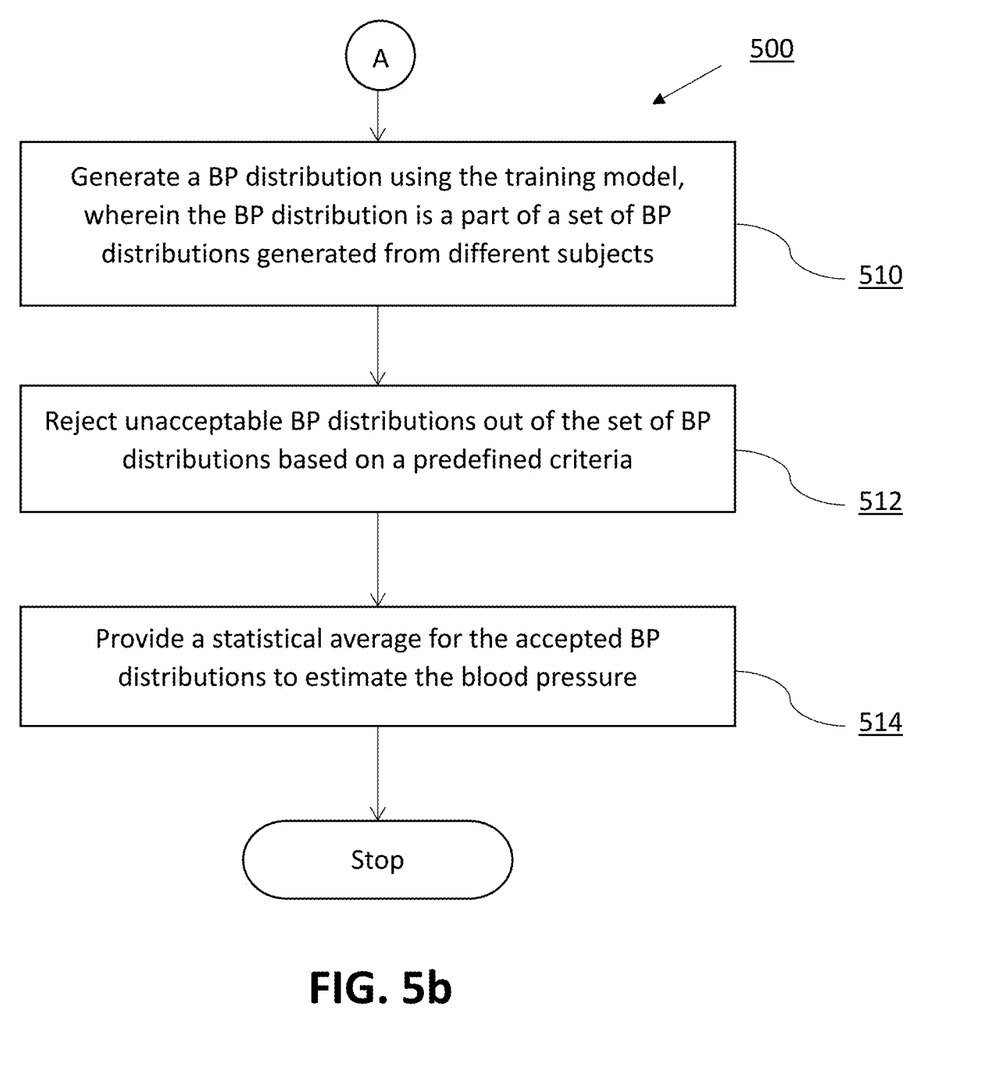

In operation, a flowchart 500 illustrating the steps involved for estimating blood pressure (BP) using photoplethysmogram (PPG) according to an embodiment of the disclosure is shown in FIG. 5a-5b. Initially at step 502, the PPG signal is captured using the PPG sensor 102. The PPG sensor 102 may be a pulse oximeter or the smartphone camera. At step 504, the captured signal is then preprocessed using the preprocessing module 108. The preprocessing include noise removal, band pass filtering and baseline correction from the captured PPG signal. In the next step 506, the plurality of features are extracted from the preprocessed PPG signal. The plurality of features are selected after analyzing their linear correlation with respect to ground truth BP in the training dataset. The plurality of features are chosen such that they have relation with BP in both oximeter and smartphone data.

At the next step 508, the training model is created for the estimation of the BP. The training model is created using the generated plurality of features and the ground truth value of the BP. At step 510, the BP distribution is generated using the training model. The BP distribution is part of a set of BP distributions generated from different subjects. Therefore at step 512, unacceptable BP distributions out of the set of BP distributions are rejected based on the predefined criteria. The predefined criteria includes clustering the estimated BP distributions and rejecting those BP distributions where there are i) multiple equally dominant clusters ii) two clusters that are too far apart or iii) unacceptable cluster formation. And finally at step 514, the statistical average is provided for the accepted BP distributions to estimate the blood pressure.

According to an embodiment of the disclosure, the estimation of the BP using the PPG signal can also be validated with the help of experimental findings as below: A dataset from the pulse oximeter and the smartphone PPG was created from non-critical patient population of a primary rural healthcare unit, an urban hospital and healthy individuals working in the lab (with the subjects' consents and ethics clearance from the Institutional Review Board). The dataset (pulse oximeter±smartphone) includes a wide range of demographic parameters such as age (45±17 years), weight (66±14 Kg) and height (162±9 cm) along with SBP (129±20 mmHg) and DBP (83±11 mmHg). Multiple data was not collected from any subject.

The pulse oximeter PPG was collected from 68 subjects for building the training model while for testing, smartphone PPG was collected from a separate set of 50 subjects. The pulse oximeter data was collected from the right hand index finger using a USB enabled fingertip pulse oximeter (Contec CMS 50D+) at 60 Hz for around a minute. Smartphone PPG was extracted from videos recorded using Nexus 5 (from the same finger with flash on) at 24 Hz for about a minute through an in-house android application. From each video frame (QCIF: 176×144 pixels), a 32×32 region from the middle was cropped and the averaged red pixel intensity was used as the PPG value. A cuff based BP measuring device exerts pressure and brings about temporary changes to blood circulation. In order to avoid this, PPG data was collected first. Ground truth BP was measured using a digital BP monitoring device from Omron immediately after the PPG data collection. All measurements were done while the user was in rest position to ensure stability in BP throughout the session.

Experimental Results

Figure 6:
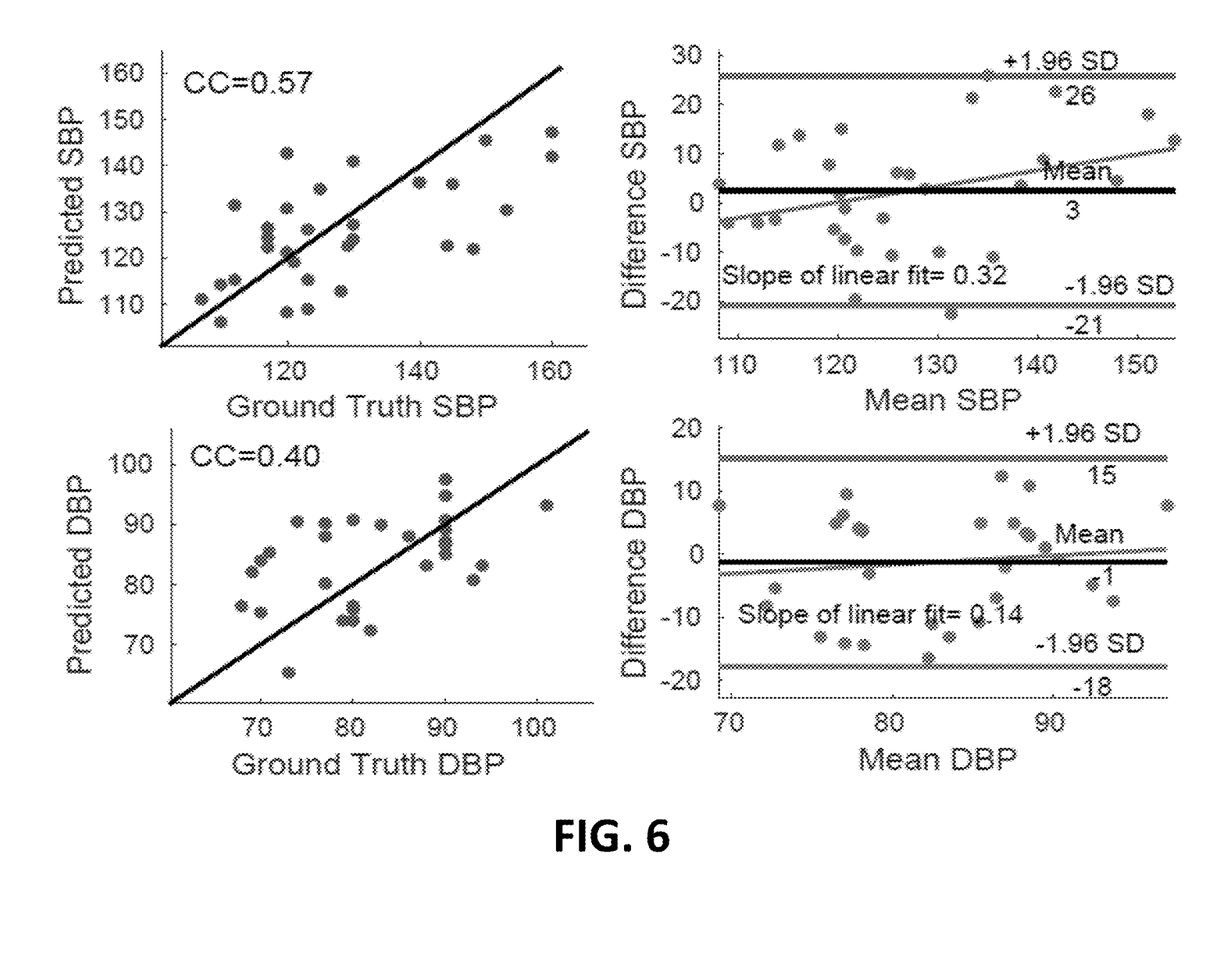
FIG. 6 shows the scatter plot of predicted and ground truth BP values with Bland Altman plot according to an embodiment of the present disclosure.

Mean Absolute Percentage Difference (MAPD), Bland Altman (BA) plots for analyzing the trend and the percentage of test data points with ≤15, ≤10 and ≤5 mmHg errors are used as performance metrics. 14 test cases were rejected by the two cluster check modules and 5 by the Cluster Formation Validity Check Module. Final results are shown in FIG. 6, through scatter plots of predicted BP with ground truth BP and BA plots. It shows that there is a good linear correlation (CC) between the predicted BPs and the ground truths. Also, the linear fit on the BA plot have small slopes for both SBP and DBP indicating that there is no particular bias in predicting high or low BP.

Further, the proposed method was compared with standard statistical averages like mean, median, trimmed mean, histogram based mode estimator that estimated BP from smartphone PPG. The histogram based mode estimator computes the median of the most frequently occurring bin, and in case of multiple bins with identical maximum frequency, an average of their medians is used. Both MAPD and the slope of the linear fit on the BA plot are low for the proposed method compared to the others that indicates good trend following along with small error. Particularly, MAPD and the slope of the BA plots are quite below 10% and 0.5 respectively, for the proposed method for both SBP and DBP unlike the others. Also the percentage of test data below 15%, 10% and 5% errors are overall high (97% and 77% data have <=15 mmHg error for SBP and DBP respectively) for the proposed method for both SBP and DBP.

Figure 7:
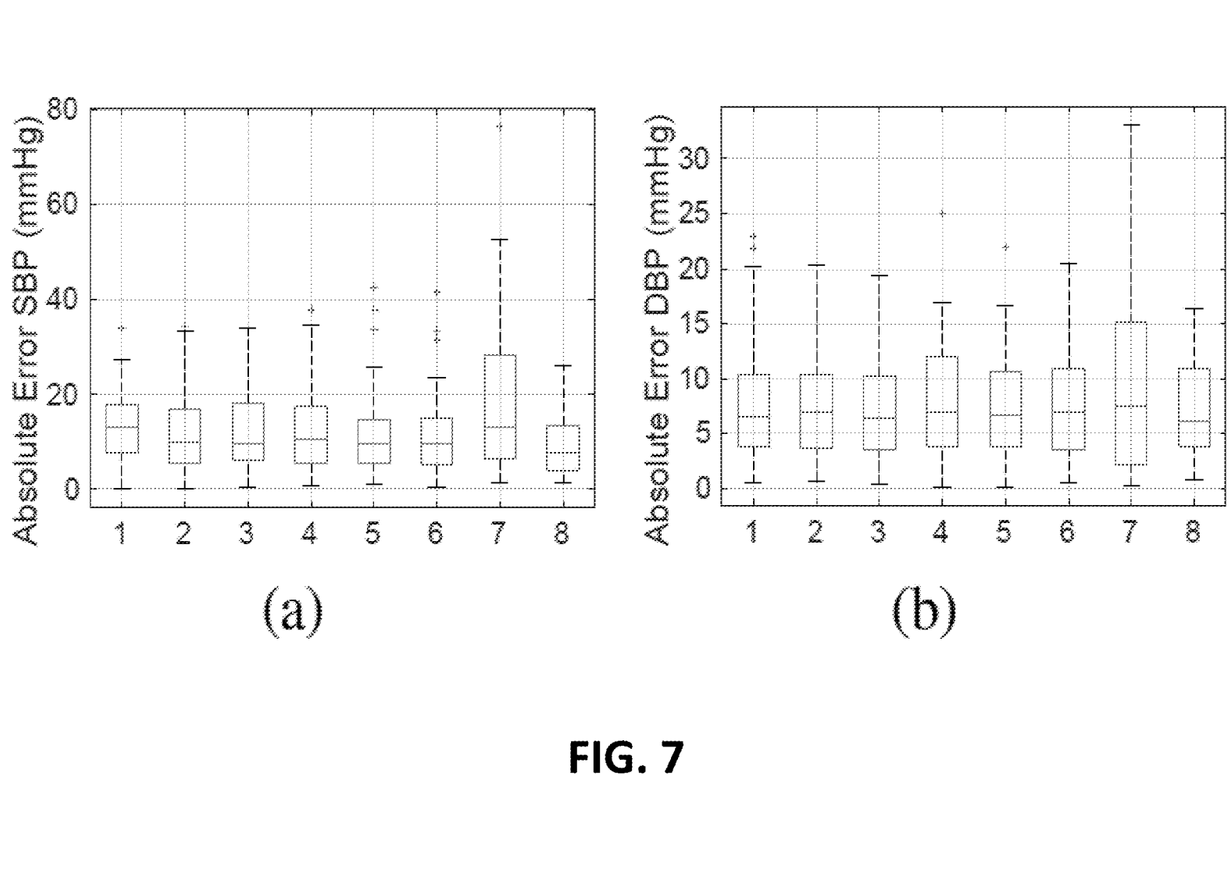
FIG. 7 shows the graphical presentation of error box plots for all methods according to an embodiment of the present disclosure.

FIG. 7 illustrates error boxplots for all methods, it clearly shows that the proposed method has the minimum median absolute error and a very small standard deviation compared to all the other methods. Also, no significant outliers are observed unlike the other methods.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein addresses unresolved problem of noisy PPG signal and high variation in the PPG signal for predicting the blood pressure. The embodiment, thus provides a method and system for estimating blood pressure using photoplethysmogram (PPG) by applying statistical post processing techniques.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for estimating blood pressure (BP) using a photoplethysmogram (PPG), the method comprising processor implemented steps of:
    capturing a PPG signal using a PPG sensor (102);
    preprocessing the PPG signal by performing band pass filtering, baseline correction, noise removal, and cycle selection based on similar pulse height and periodicity to take care of changes in PPG signal amplitude due to variable finger pressure and discontinuities due to motion artifacts, wherein the band pass filtering is performed in the range of 0.75-8 Hz;
    extracting a plurality of features from the preprocessed PPG signal, wherein the plurality of features are extracted by evaluating linear correlation between the plurality of features and ground truth BP in a training dataset, wherein the ground truth BP is measured using a digital BP monitoring device immediately after capturing the PPG signal, and wherein the plurality of features extracted include $T_s$, $T_s/T_d$, $A_s/A_d$, and $1/T_s^2$, and wherein $T_s$ is systolic upstroke time, $T_d$ is diastolic time, $A_s$ is systolic area, $A_d$ is diastolic area of the PPG signal;

creating a training model for estimating the BP using the plurality of features of the PPG signal and a ground truth value of the BP, wherein the training model is created using a gradient descent learning based linear regression;

generating a BP distribution using the training model, wherein the BP distribution is part of a set of BP distributions generated from different subjects; and post processing the set of BP distributions to estimate the BP, wherein the post processing comprises:

rejecting unacceptable BP distributions out of the set of BP distributions based on a predefined criteria, wherein the predefined criteria includes clustering the set of BP distributions into clusters of similar BP based on probability density and rejecting those BP distributions where there are i) multiple equally dominant clusters ii) two clusters that are too far apart or iii) unacceptable cluster formation, wherein the multiple equally dominant clusters are the clusters with a range of cluster populousness below a threshold, wherein the set of BP distributions is checked for the multiple equally dominant clusters when number of clusters in systolic BP or diastolic BP is greater than or equal to three, to identify if too many small clusters exist uniformly all over the set of BP distributions, wherein when the set of BP distributions comprises two clusters, then distribution width between the two clusters is checked to identify if the clusters are too far apart, and wherein the clusters of similar BP are determined based on best Bayesian Information Criterion (BIC); and providing a statistical average for the accepted BP distributions to estimate the BP.

2. The method of claim 1, wherein a half range-mode is used for calculating the statistical average.

3. The method of claim 1, wherein the PPG sensor is a pulse oximeter or a smartphone camera.

4. A system for estimating blood pressure (BP) using a photoplethysmogram (PPG), the system comprising:

a PPG sensor (102) configured to capture a PPG signal;

a memory (104);

a processor (106) in communication with the memory (104);

a preprocessing module (108), coupled to the processor (106), configured to preprocess the captured PPG signal by performing band pass filtering, baseline correction, noise removal, and cycle selection based on similar pulse height and periodicity to take care of changes in PPG signal amplitude due to variable finger pressure and discontinuities due to motion artifacts, wherein the band pass filtering is performed in the range of 0.75-8 Hz;

a feature selection module (110), coupled to the processor (106), configured to extract a plurality of features from the preprocessed PPG signal, wherein the plurality of features are extracted by evaluating linear correlation between the plurality of features and ground truth BP in a training dataset, wherein the ground truth BP is measured using a digital BP monitoring device immediately after capturing the PPG signal, and wherein the plurality of features extracted include $T_s$, $T_s/T_d$, $A_s/A_d$, and $1/T_s^2$, and wherein $T_s$ is systolic upstroke time, $T_d$ is diastolic time, $A_s$ is systolic area, $A_d$ is diastolic area of the PPG signal;

a training model generation module (112), coupled to the processor (106), configured to create a training model for estimating the BP using the plurality of features and a ground truth value of the BP, wherein the training model is created using a gradient descent learning based linear regression;

a regression module (114), coupled to the processor (106), configured to generate a BP distribution using the training model, wherein the BP distribution is part of a set of BP distributions generated from different subjects; and a post-processing module (116), coupled to the processor (106), configured to post process the set of BP distributions to:

reject unacceptable BP distributions out of the set of BP distributions based on a predefined criteria, wherein the predefined criteria includes clustering the set of BP distributions into clusters of similar BP based on probability density and rejecting those BP distributions where there are i) multiple equally dominant clusters ii) two clusters that are too far apart or iii) unacceptable cluster formation, wherein the multiple equally dominant clusters are the clusters with a range of cluster populousness below a threshold, wherein the set of BP distributions is checked for the multiple equally dominant clusters when number of clusters in systolic BP or diastolic BP is greater than or equal to three, to identify if too many small clusters exist uniformly all over the set of BP distributions, wherein when the set of BP distributions comprises two clusters, then distribution width between the two clusters is checked to identify if the clusters are too far apart, and wherein the clusters of similar BP are determined based on best Bayesian Information Criterion (BIC); and provide a statistical average for the accepted BP distributions to estimate the BP.

5. The system of claim 4, wherein the PPG sensor (102) is a pulse oximeter or a smartphone camera.

6. One or more non-transitory computer readable information medium having embodied thereon a computer program for executing a method for estimating blood pressure (BP) using a photoplethysmogram (PPG), wherein the method comprises:

capturing a PPG signal using a PPG sensor (102);

preprocessing the PPG signal by performing band pass filtering, baseline correction, noise removal, and cycle selection based on similar pulse height and periodicity to take care of changes in PPG signal amplitude due to variable finger pressure and discontinuities due to motion artifacts, wherein the band pass filtering is performed in the range of 0.75-8 Hz;

extracting a plurality of features from the preprocessed PPG signal, wherein the plurality of features are extracted by evaluating linear correlation between the plurality of features and ground truth BP in a training dataset, wherein the ground truth BP is measured using a digital BP monitoring device immediately after capturing the PPG signal, and wherein the plurality of features extracted include $T_s$, $T_s/T_d$, $A_s/A_d$, and $1/T_s^2$, and wherein $T_s$ is systolic upstroke time, $T_d$ is diastolic time, $A_s$ is systolic area, $A_d$ is diastolic area of the PPG signal;

creating a training model for estimating the BP using the plurality of features of the PPG signal and a ground truth value of the BP, wherein the training model is created using a gradient descent learning based linear regression;

generating a BP distribution using the training model, wherein the BP distribution is part of a set of BP distributions generated from different subjects; and post processing the set of BP distributions to estimate the BP, wherein the post processing comprises:

rejecting unacceptable BP distributions out of the set of BP distributions based on a predefined criteria, wherein the predefined criteria includes clustering the set of BP distributions into clusters of similar BP based on probability density and rejecting those BP distributions where there are i) multiple equally dominant clusters ii) two clusters that are too far apart or iii) unacceptable cluster formation, wherein the multiple equally dominant clusters are the clusters with a range of cluster populousness below a threshold, wherein the set of BP distributions is checked for the multiple equally dominant clusters when number of clusters in systolic BP or diastolic BP is greater than or equal to three, to identify if too many small clusters exist uniformly all over the set of BP distributions, wherein when the set of BP distributions comprises two clusters, then distribution width between the two clusters is checked to identify if the clusters are too far apart, and wherein the clusters of similar BP are determined based on best Bayesian Information Criterion (BIC); and providing a statistical average for the accepted BP distributions to estimate the BP.

* * * * *